US00PP31865P2

(12) United States Plant Patent
Wood

(10) Patent No.: US PP31,865 P2
(45) Date of Patent: Jun. 16, 2020

(54) ***PHILADELPHUS* PLANT NAMED 'SMNPVG'**

(50) Latin Name: *Philadelphus coronarius*
Varietal Denomination: SMNPVG

(71) Applicant: Timothy D Wood, Spring Lake, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,067

(22) Filed: Feb. 14, 2019

(51) Int. Cl.
*A01H 5/02* (2018.01)
*A01H 6/48* (2018.01)

(52) U.S. Cl.
USPC ..... Plt./226

(58) Field of Classification Search
USPC ..... Plt./226
CPC ..... A01H 5/02; A01H 5/00; A01H 6/48
See application file for complete search history.

(56) References Cited

PUBLICATIONS

Spring Meadow Flowering Shrubs 2018-2019, retrieved on Oct. 8, 2019, retrieved at https://springmeadownursery.com/files/resource_files/2018-2019_SMN_Catalog_1-47.pdf cover page, pp. 1-9,17 and https://springmeadownursery.com/files/resource_files/2018-2019_SMN_Catalog_48-100.pdf, p. 70. (Year: 2019).*

* cited by examiner

*Primary Examiner* — June Hwu
(74) *Attorney, Agent, or Firm* — Cassandra Bright

(57) ABSTRACT

A new and distinct *Philadelphus* cultivar named 'SMNPVG' is disclosed, characterized by a very upright, columnar shape, and are well suited to container production. Foliage is thick and durable. Flowers are uniquely arranged in vertical stacks. The new variety is a *Philadelphus*, normally used for outdoor ornamental purposes.

2 Drawing Sheets

Latin name of the genus and species: *Philadelphus coronarius*.

Variety denomination: 'SMNPVG'.

BACKGROUND OF THE INVENTION

The new *Philadelphus* cultivar is a product of a planned breeding program conducted by the inventor, Timothy Wood, in Grand Haven, Mich. The objective of the breeding program was to develop new forms of flowers, and new habits. The open-pollination resulting in this new variety was made during Summer of 2011.

The seed parent is an unnamed *Philadelphus coronarius*. The new variety was selected in Spring of 2014 by the inventor in a group of seedlings resulting from the 2011 open pollination, in a nursery in Grand Haven, Mich.

Asexual reproduction of the new cultivar has been performed by softwood cuttings. This was first performed at the same nursery in Grand Haven, Mich. in 2014, and has shown that the unique features of this cultivar are stable and reproduced true to type in multiple successive generations. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'SMNPVG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNPVG' These characteristics in combination distinguish 'SMNPVG' as a new and distinct *Philadelphus* cultivar:

1. Very upright, columnar shape.
2. Flowers are uniquely stacked vertically, rather than clustered.
3. Excellent performance as a container plant.
4. Thick, durable foliage.

Plants of the new cultivar 'SMNPVG' are similar to plants of the seed parent in most horticultural characteristics; however, plants of the new cultivar 'SMNPVG' differ in the following;

1. The new variety is vertical and columnar, while the seed parent is more rounded.
2. The new variety has thicker leaves, while the seed parent has more delicate leaves.

COMMERCIAL COMPARISON

Plants of the new cultivar 'SMNPVG' are comparable to the commercial variety *Philadelphus* 'Belle Etoile', unpatented. The two *Philadelphus* varieties are similar in most horticultural characteristics; however, the new variety 'SMNPVG' differs in the following;

1. The new variety is vertical; this comparator has a sprawling, arching shape.

2. The new variety has smaller flowers than this comparator.
3. The new variety has larger, darker green foliage than this comparator.

BRIEF DESCRIPTION OF THE PHOTOGRAPHS

Figure 1:
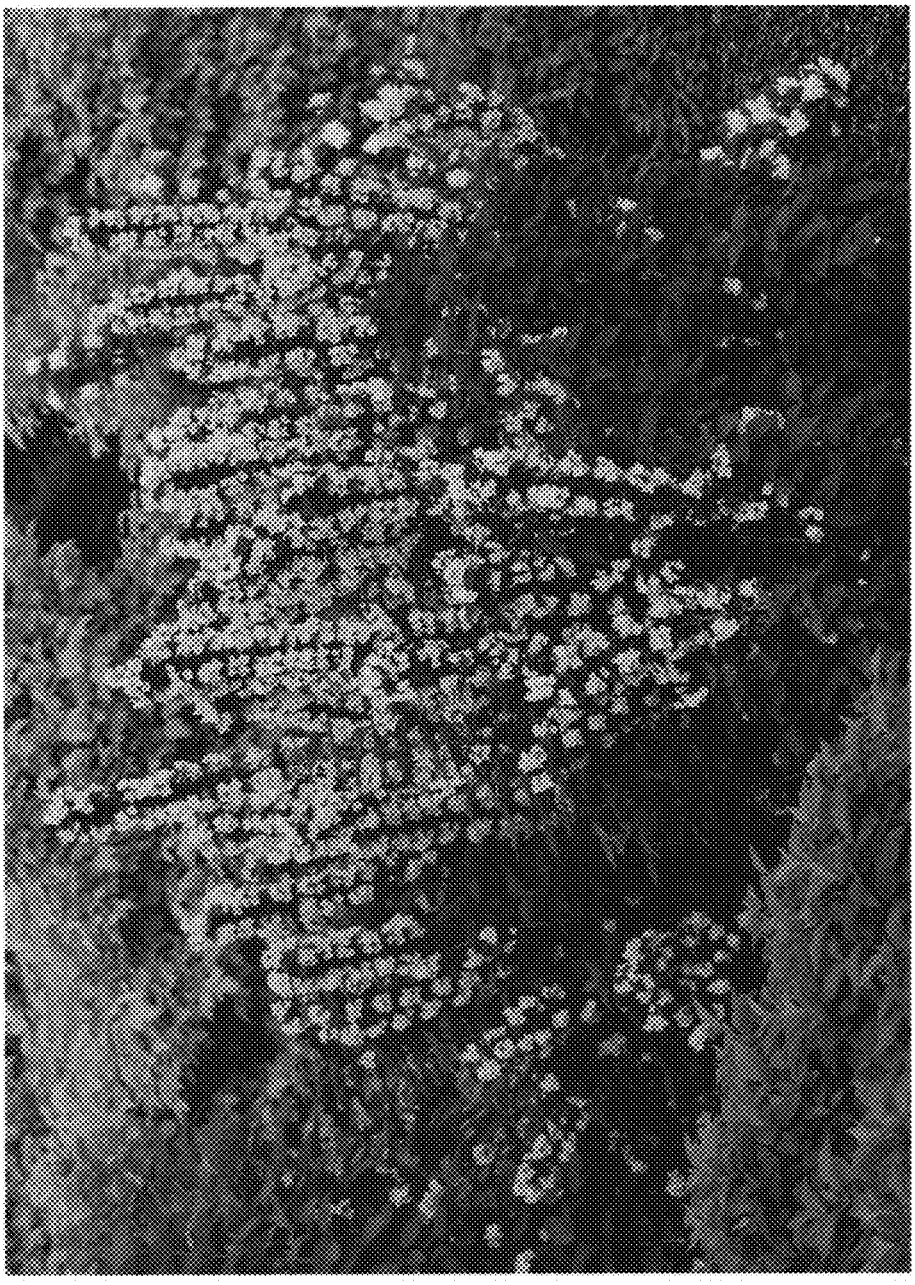

The accompanying photograph in FIG. 1 illustrates in full color a typical plant of 'SMNPVG' in the ground. Age of the plant photographed is approximately 2-3 years old from a rooted cutting.

Figure 2:
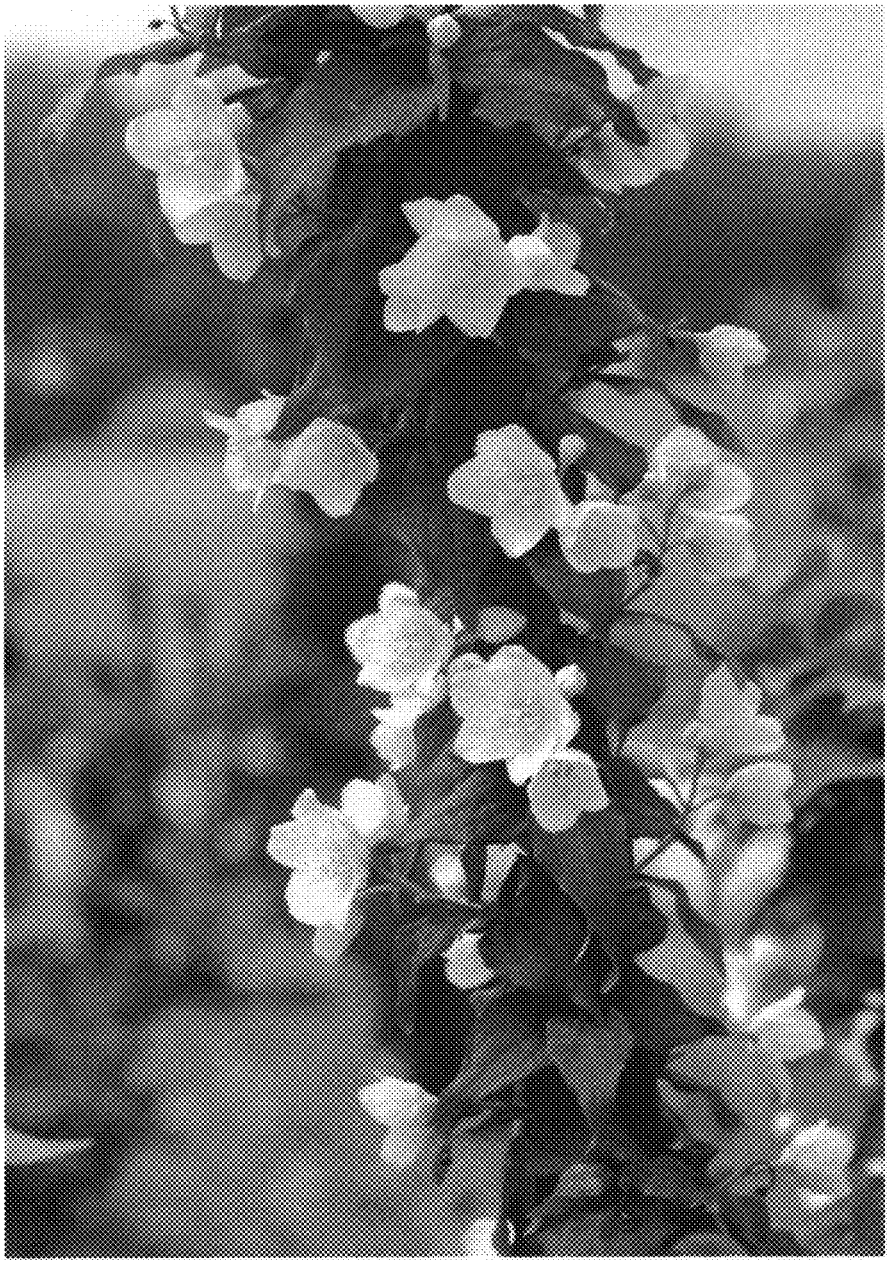

FIG. 2 illustrates a close up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNPVG' plants grown in a poly house during August 2017, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Philadelphus coronarius* 'SMNPVG'.

PROPAGATION

Type of propagation typically used: Softwood cuttings.
Time to initiate roots: About 2 weeks.
Time to produce a rooted cutting: About 2 months.
Root description: Thin to thick, fibrous, dense, freely branching. White to brown in color, not accurately measured with R.H.S. Chart.

PLANT

Age of plant described: 2-3 years old from a rooted cutting.
Container size: 3 gallon container.
Overall plant shape: Upright, columnar.
Growth habit: Upright.
Plant spread: 46 cm.
Plant height: 71 cm.
Growth rate: Good.
Plant vigor: Very vigorous.
Branching habit: Lots of basal branching, very upright. Some pinching required.
Length of primary lateral branches: 42 cm.
Diameter of lateral branches: 4 mm.
Quantity of lateral branches: 15.
Stem:
- *Color*.—New growth: RHS Green 143C. Old growth: RHS Greyed-Brown 199B.
- *Shape*.—Round.
- *Strength*.—Strong.
- *Aspect angle*.—Very upright.
- *Pubescence*.—On new growth.

Internode length: 2.5 cm.

FOLIAGE

Leaf:
- *Arrangement*.—Opposite, single.
- *Average length*.—5.5cm.
- *Average width*.—3.5 cm.
- *Shape of blade*.—Ovate.
- *Apex*.—Acuminate.
- *Base*.—Obtuse.
- *Margin*.—Serrate.
- *Texture of top surface*.—Leathery.
- *Texture of bottom surface*.—Rough, distinct veins.
- *Color*.—Young foliage upper side: RHS Green 137C. Young foliage under side: RHS Yellow-Green 146B. Mature foliage upper side: RHS Green 137C. Mature foliage under side: RHS Yellow-Green 147B.
- *Venation*.—Type: Pinnate. Venation color upper side: RHS Yellow-Green N144C. Venation color under side: RHS Yellow-Green N144C.
- *Petiole*.—Length: 5 mm. Diameter: 3 mm. Texture, upper side: Slightly pubescent. Texture, under side: Smooth. Color, upper side: RHS Yellow-Green N144C. Color, under side: RHS Yellow-Green N144C.

FLOWER

Natural flowering season: Spring.
Inflorescence form: Raceme.
Flowers and buds per inflorescence: 2-7.
Inflorescence size:
- *Width*.—3.5 to 6.0 cm.
- *Height*.—20 to 40 cm.

Inflorescence arrangement: 1 to 6 Racemes occurring per node, resulting in a stacked arrangement of inflorescences.
Individual flowers:
- *Shape*.—Rotate.
- *Type*.—Rotate.
- *Diameter*.—5 mm.
- *Length*.—2 cm.
- *Aspect*.—Upright and outwards.
- *Persistence*.—Self-cleaning.
- *Fragrance*.—Light, sweet, earthy.
- *Lastingness of blooms*.—3-5 days.

Petals:
- *Arrangement*.—Rotate.
- *Number*.—4 or 5.
- *Shape*.—Orbicular, widely elliptic.
- *Margin*.—Entire.
- *Tip shape*.—Obtuse.
- *Base shape*.—Obtuse/truncate.
- *Length*.—1 cm.
- *Width*.—8 mm.
- *Texture*.—Upper: Smooth. Lower: Smooth.
- *Color*.—When opening: Upper surface: RHS White NN155C. Under surface: RHS White NN155C. Fully opened: Upper surface: RHS White NN155C. Under surface: RHS White NN155C.

Bud:
- *Shape*.—Ovoid.
- *Length*.—1 cm.
- *Diameter*.—6 mm.
- *Color*.—RHS White NN155C.

Sepals:
*Appearance*.—Tear-drop shaped.
*Arrangement*.—Cruciform.
*Shape*.—Tear-drop.
*Tip shape*.—Very acute.
*Base shape*.—Truncate.
*Margin*.—Entire.
*Quantity per flower*.—4.
*Length*.—5 mm.
*Width*.—4 mm.
*Texture*.—Upper: Smooth. Lower: Smooth.
*Color*.—Upper: RHS Yellow-Green 145C. Lower: RHS Yellow-Green 145C.

Calyx:
*Shape*.—Cupulate.
*Length*.—2 mm.
*Diameter*.—5 mm.

Pedicel:
*Length*.—5 mm.
*Diameter*.—1 mm.
*Texture*.—Smooth.
*Angle*.—0-45°.
*Color*.—RHS Green 143B.
*Strength*.—Good.

REPRODUCTIVE ORGANS

Stamens:
*Number*.—About 20.
*Filament length*.—3.5 mm.
*Filament color*.—RHS White 155C.

Anthers:
*Shape*.—Globular.
*Length*.—1 mm.
*Color*.—RHS Greyed-Yellow 161B.
*Pollen*.—Amount: Some. Color: RHS Greyed-Yellow 161B.

Pistil:
*Number*.—1.
*Length*.—5 mm.
*Style*.—Length: 2 mm. Color: RHS White NN155C.

Stigma:
*Shape*.—Double-lobed.
*Color*.—RHS White NN155C.
*Ovary color*.—RHS White NN155C.

OTHER CHARACTERISTICS

Fruits and seeds: Not observed to date.
Disease/pest resistance: Neither resistance nor susceptibility to normal diseases and pests of *Philadelphus* observed.
Temperature range: Observed to tolerate a temperature range from −28° C. to 35° C. Root hardy to −28C, top of the plant does die back to the ground.

What is claimed is:

1. A new and distinct cultivar of *Philadelphus* plant named 'SMNPVG' as herein illustrated and described.

* * * * *